United States Patent [19]
Sakamoto et al.

[11] Patent Number: 5,785,821
[45] Date of Patent: Jul. 28, 1998

[54] PROCESS FOR THE PRODUCTION OF ACRYLIC ACID

[75] Inventors: Kazuhiko Sakamoto; Sei Nakahara; Takahiro Takeda; Masatoshi Ueoka; Yohji Akazawa, all of Himeji, Japan

[73] Assignee: Nippon Shokubai Co., Ltd., Osaka, Japan

[21] Appl. No.: 759,219

[22] Filed: Dec. 5, 1996

[30] Foreign Application Priority Data

Dec. 5, 1995 [JP] Japan ................... 7-316182

[51] Int. Cl.[6] ................... B01D 3/34
[52] U.S. Cl. ................... 203/57; 562/600
[58] Field of Search ................... 203/57, 61, 98; 562/600

[56] References Cited

U.S. PATENT DOCUMENTS

| | | | |
|---|---|---|---|
| 3,666,632 | 5/1972 | Honda et al. | 203/56 |
| 3,689,541 | 9/1972 | Sennewald et al. | 260/526 |
| 3,692,829 | 9/1972 | Sennewald et al. | 260/526 |
| 3,855,081 | 12/1974 | Brown et al. | 203/91 |
| 3,859,175 | 1/1975 | Ohrui et al. | 203/46 |
| 4,156,633 | 5/1979 | Horlenko et al. | 203/93 |
| 4,166,774 | 9/1979 | Wagner et al. | 203/82 |
| 4,199,410 | 4/1980 | Ohrui et al. | 203/49 |
| 5,315,037 | 5/1994 | Sakamoto et al. | 562/545 |

FOREIGN PATENT DOCUMENTS

| | | |
|---|---|---|
| 3429391 | 2/1985 | Germany. |
| 4634692 | 10/1971 | Japan. |
| 5246941 | 9/1992 | Japan. |
| 2146636 | 4/1985 | United Kingdom. |

*Primary Examiner*—Nina Bhat
*Attorney, Agent, or Firm*—Sherman and Shalloway

[57] ABSTRACT

The present invention provides an improved process for production of acrylic acid by subjecting propylene and/or acrolein to catalytic gas-phase oxidation with a molecular oxygen-containing gas. In the process, the mixed gas obtained by the catalytic gas-phase oxidation is contacted with an aqueous collecting agent containing acrylic acid, acetic acid and a poorly-soluble-in-water solvent, to form an aqueous acrylic acid solution; and the aqueous acrylic acid solution is subjected to azeotropic distillation in the presence of a poorly-soluble-in-water solvent to remove by-products and obtain high-purity acrylic acid.

5 Claims, 1 Drawing Sheet

PROCESS FOR THE PRODUCTION OF ACRYLIC ACID

The present invention relates to a process for producing acrylic acid at a high purity by separating by-products, particularly acetic acid efficiently from a mixed gas obtained by subjecting propylene and/or acrolein to catalytic gas-phase oxidation with a molecular oxygen-containing gas. More particularly, the present invention relates to a process for producing high-purity acrylic acid by contacting said mixed gas with an aqueous solution containing acrylic acid, acetic acid and a poorly-soluble-in-water solvent, to form an aqueous acrylic acid solution, and then subjecting the aqueous acrylic acid solution to azeotropic distillation in the presence of a poorly-soluble-in-water solvent to remove by-products.

In catalytic gas-phase oxidation of propylene and/or acrolein with a molecular oxygen-containing gas in the presence of an oxidation catalyst, there is obtained, as the reaction product, a mixed gas containing acrylic acid (an intended compound) and by-products (e.g. acetic acid). In conventional industrial processes for production of acrylic acid by catalytic gas-phase oxidation of propylene and/or acrolein with a molecular oxygen-containing gas, a mixed gas obtained by the catalytic gas-phase oxidation is absorbed by water in an acrylic acid-collecting tower to obtain an aqueous solution containing acrylic acid and by-products (e.g. acetic acid), followed by distillation of the aqueous solution for separation of acrylic acid and subsequent purification of the separated acrylic acid to obtain a product.

For example, Japanese Patent Application Kokai (Laid-Open) No. 246941/1993 discloses a process in which the acetic acid solution obtained is circulated for reuse as an absorbent in the acrylic acid-collecting tower. In the process, however, since a solvent soluble in water in a non-negligible amount is used as a solvent for azeotropic distillation, a step is necessary for recovery of the solvent from the aqueous phase distilled off from the azeotropic distillation tower, requiring, besides the azeotropic distillation tower, a distillation tower for recovery of the solvent. Further in the process, since the acetic acid solution circulated for reuse as an absorbent contains no solvent and substantially no acrylic acid, the collection efficiency in the acrylic acid-collecting tower is insufficient.

Japanese Patent Publication No. 34691/1971 discloses a process which uses heptane as a solvent for azeotropic distillation. In the process, however, the aqueous phase distilled off from the azeotropic distillation tower contains acrylic acid in an amount of only 0.5% by weight or less and, moreover, there is no description on the circulation of the aqueous phase for reuse. Further in the process, the separation of acetic acid and water at the tower bottom is insufficient, making it difficult to obtain a high-purity acrylic acid product.

The object of the present invention lies in providing a high-quality acrylic acid product which has been unobtainable with conventional processes, by, in the production of acrylic acid by catalytic gas-phase oxidation of propylene and/or acrolein, treating the mixed gas formed by the catalytic gas-phase oxidation, by a noble method.

To achieve the above object, the present invention provides a process for production of acrylic acid, which comprises:

introducing, into an acrylic acid-collecting tower, a mixed gas obtained by subjecting propylene and/or acrolein to catalytic gas-phase oxidation with a molecular oxygen-containing gas, and contacting the mixed gas with an aqueous collecting agent containing 0.5–5.0% by weight of acrylic acid, 3.0–10.0% by weight of acetic acid and 0.01–0.5% by weight of a poorly-soluble-in-water solvent, to form an aqueous acrylic acid solution, introducing the aqueous acrylic acid solution into an azeotropic distillation tower and subjecting the solution to azeotropic distillation using a poorly-soluble-in-water solvent, to obtain, from the tower bottom, acrylic acid substantially free from acetic acid, water or the poorly-soluble-in-water solvent and distil off, from the tower top, a mixture containing acetic acid, acrylic acid, water and the poorly-soluble-in-water solvent, introducing the mixture distilled off from the tower top, into a storage tank to separate it into an organic phase composed substantially of the poorly-soluble-in-water solvent and an aqueous phase containing acrylic acid, acetic acid, the poorly-soluble-in-water solvent and water, and circulating the organic phase into the azeotropic distillation tower.

The present invention also provides, as one preferred embodiment of the above process, a process wherein the above-mentioned aqueous phase separated in the storage tank is circulated into the acrylic acid-collecting tower to use it as an acrylic acid-collecting agent.

According to the above process of the present invention, acrylic acid can be collected at a high efficiency by introducing, into an acrylic acid-collecting tower, a mixed gas obtained by catalytic gas-phase oxidation of propylene and/or acrolein with a molecular oxygen-containing gas; and by subjecting the aqueous acrylic acid solution obtained by the above collection, to azeotropic distillation in an azeotropic distillation tower, a high-purity acrylic acid product can be obtained from the bottom of the distillation tower.

Figure 1:
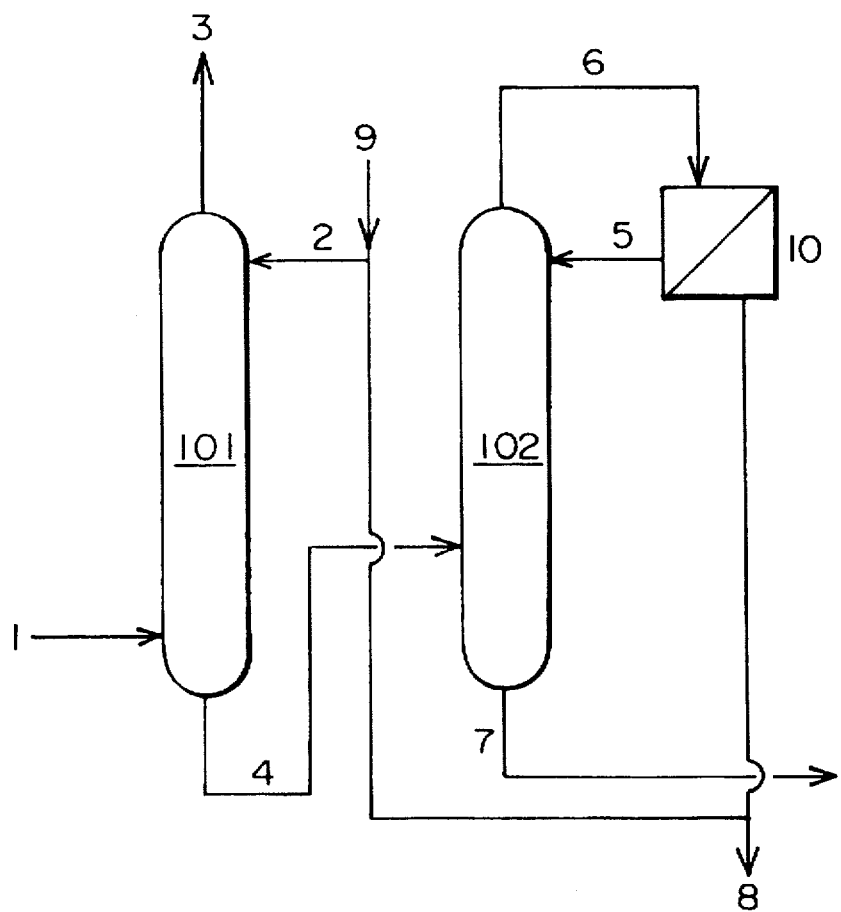
FIG. 1, which is an accompanying drawing, is a flow sheet showing a typical embodiment of the present invention. The present invention is hereinafter described specifically referring to FIG. 1.

The mixed gas containing acrylic acid and by-products (e.g. acetic acid), obtained by catalytic gas-phase oxidation of propylene and/or acrolein with a molecular oxygen-containing gas in the presence of an oxidation catalyst, is introduced into an acrylic acid-collecting tower 101 through a line 1, and is contacted with an aqueous collecting agent containing acrylic acid, acetic acid and a poorly-soluble-in-water solvent, introduced into the tower 101 through a line 2, to form an aqueous acrylic acid solution containing acrylic acid and by-products (e.g. acetic acid). The mixed gas after contact with the aqueous collecting agent leaves the acrylic acid-collecting tower 101 through a line 3, and is recycled into an oxidation reaction step or discharged into the atmosphere as a waste gas via a combustion step.

The aqueous acrylic acid solution leaves the acrylic acid-collecting tower 101 through a line 4, is introduced into an azeotropic distillation tower 102, and is subjected therein to azeotropic distillation with a poorly-soluble-in-water solvent fed through a line 5 as a solvent for azeotropic distillation. From the bottom of the tower 102 through a line 7 is obtained acrylic acid; and from the top of the tower 102 through a line 6 is distilled off a mixture containing acetic acid, acrylic acid, water and the solvent. The distilled mixture is introduced into a storage tank 10 through the line 6 and separated therein into (1) an organic phase composed substantially of the solvent alone and (2) an aqueous phase containing acrylic acid, acetic acid, the poorly-soluble-in-water solvent and water. The organic phase is circulated into the azeotropic distillation tower 102 through the line 5. Preferably, the distilled mixture is allowed to stay in the storage tank 10 for 0.5–2 hours for complete separation of the organic phase and the aqueous phase.

The aqueous phase separated in the storage tank 10 is preferably circulated into the acrylic acid-collecting tower 101 through the line 2 to be used as an acrylic acid-collecting agent. Optionally, part of the aqueous phase may be discharged out of the system through a line 8.

The mixed gas introduced into the acrylic acid-collecting tower 101, i.e. the mixed gas obtained by catalytic gas-phase oxidation of propylene and/or acrolein with a molecular oxygen-containing gas, preferably contains acrylic acid, acetic acid and steam in amounts of 10–20% by weight, 0.2–1.0% by weight and 5–15% by weight, respectively. These components of the mixed gas are collected in the acrylic acid-collecting tower 101 in the form of an aqueous acrylic acid solution.

The aqueous acrylic acid solution generally contains 50–80% by weight of acrylic acid, 1–5% by weight of acetic acid and 20–40% by weight of water under the ordinary conditions of acrylic acid synthesis. The proportions of these components in the aqueous acrylic acid solution are not restricted to the above ranges and vary depending upon the operating conditions of the oxidation reactor and/or the acrylic acid-collecting tower.

The aqueous collecting agent used in the acrylic acid-collecting tower 101 must contain acrylic acid, acetic acid and a poorly-soluble-in-water solvent in amounts of 0.5–5.0% by weight, 3.0–10.0% by weight and 0.01–0.5% by weight, respectively. An aqueous collecting agent containing 1.0–2.0% by weight of acrylic acid, 4.0–8.0% by weight of acetic acid and 0.01–0.3% by weight of a poorly-soluble-in-water solvent is particularly preferred. With an aqueous collecting agent containing less than 0.5% by weight of acrylic acid or less than 3.0% by weight of acetic acid, there is no improvement of acrylic acid collectability in the acrylic acid-collecting tower. When the acrylic acid concentration in the aqueous collecting agent is more than 5.0% by weight and/or the acetic acid concentration in the agent is more than 10.0% by weight, the monomer polymerization in the azeotropic distillation tower increases significantly and the long-term continuous operation of the apparatus becomes difficult and, in order to carry out the continuous operation, a large amount of a polymerization inhibitor is required, inviting poor economy. The temperature at the top of the acrylic acid-collecting tower is preferably 50°–70° C.

The aqueous collecting agent is generally fed into the acrylic acid-collecting tower 101 through a line 9 in the form of an aqueous solution prepared so as to have the above composition. In some cases, however, the aqueous phase separated in the storage tank 10 is circulated into the acrylic acid-collecting tower 101 through the line 2 and is used as the aqueous collecting agent. In that case, the aqueous phase is circulated into the collecting tower 101 in an any desired proportion, preferably in a proportion of 50–90% by weight. When 50–90% by weight of the aqueous phase is circulated, the shortage of the collecting agent is made up with a fresh collecting agent through the line 9. Meanwhile, that portion of the aqueous phase which is separated in the storage tank 10 and which is not circulated into the collecting tower 101, i.e. 10–50% by weight of the aqueous phase is discharged out of the system as a waste water through the line 8. Therefore, by circulating more than half of the aqueous phase into the collecting tower 101, the amount of the waste water can be decreased. In the present invention, since the aqueous phase per se can be used as the aqueous collecting agent, it is not necessary to recover, by distillation, the poorly-soluble-in-water solvent contained in the aqueous phase in a very small amount.

The aqueous acrylic acid solution formed in the collecting tower 101 is subjected to azeotropic distillation in the azeotropic distillation tower 102 in the presence of a poorly-soluble-in-water solvent. The acrylic acid drawn out from the bottom of the azeotropic distillation tower 102 is sent to an esterification step through the line 7 and is used as a raw material for acrylic acid ester, per se or after the purification step.

The poorly-soluble-in-water solvent used as a solvent for azeotropic distillation in the present invention is a solvent having a solubility in water at room temperature, of 0.5% by weight or less, preferably 0.2% by weight or less. The solvent is specifically at least one solvent selected from the group consisting of aliphatic hydrocarbons having 7–8 carbon atoms, aromatic hydrocarbons having 7–8 hydrocarbons and halogenated hydrocarbons having 2–6 carbon atoms. More specifically, the aliphatic hydrocarbons having 7–8 carbon atoms include heptane, heptene, cycloheptane, cycloheptene, cycloheptadiene, cycloheptatriene, methylcyclohexane, ethylcyclopentane, dimethylcyclohexane, ethylcyclohexane, etc. The aromatic hydrocarbons having 7–8 carbon atoms include toluene, ethylbenzene, xylene, etc. The halogenated hydrocarbons having 2–6 carbon atoms include tetrachloroethylene, trichloropropene, dichlorobutane, chloropentane, chlorohexane, chlorobenzene, etc. Preferred as the poorly-soluble-in-water solvent is at least one solvent selected from the group consisting of heptane, dimethylcylohexane, ethylcyclohexane, toluene, ethylbenzene and xylene. More preferred is at least one solvent selected from the group consisting of heptane, toluene and ethylbenzene.

The present invention has the following meritorious effects.

(1) An aqueous solution containing acetic acid, acrylic acid and a solvent for azeotropic distillation is used as a collecting agent for collection of acrylic acid from a gas mixture; as a result, the acrylic acid collectability is high as compared with those in conventional processes using, as said collecting agent, water or an aqueous solution containing water alone.

(2) The aqueous phase of the distillate from the azeotropic distillation tower contains acrylic acid and acetic acid; therefore, when the aqueous phase per se is used as said collecting agent, neither solvent recovery step nor acetic acid separation step is required and high-purity acrylic acid is obtained in one step.

(3) Since the solvent for azeotropic distillation can be removed completely at the bottom of the azeotropic distillation tower, there is no mixing of the solvent into product acrylic acid.

(4) Since low-boiling impurities are distilled off from the azeotropic distillation tower and are not refluxed thereinto, monomer polymerization in the tower is inhibited.

The following Examples and Comparative Examples describe the present invention specifically.

EXAMPLE 1

Propylene was subjected to catalytic gas-phase oxidation with a molecular oxygen-containing gas in the presence of an oxidation catalyst to obtain a mixed gas containing 0.680 kg/h of acrylic acid, 0.014 kg/h of acetic acid and 0.450 kg/h of water. An operation of collecting acrylic acid from the mixed gas was conducted using (1) an acrylic acid-collecting tower which was filled with cascade mini-rings (inside diameter: 14 mm) in a height of 6,000 mm and which was provided with a gas-releasing pipe at the top, a raw material-feeding pipe at the lower portion, and a bottom solution-drawing pipe at the bottom, and (2) an aqueous collecting agent containing 4.8% by weight of acrylic acid, 8.0% by weight of acetic acid and 0.01% by weight of octene.

In a steady-state operation, an aqueous solution containing 0.674 kg/h of acrylic acid was obtained from the tower bottom and a gas containing 0.006 kg/h of acrylic acid was released from the tower top.

COMPARATIVE EXAMPLE 1

An operation of collecting acrylic acid from the mixed gas mentioned in Example 1 was conducted in the same manner as in Example 1 except that the aqueous collecting agent used in Example 1 was replaced by an aqueous solution containing 8.0% by weight of acetic acid but containing neither acrylic acid nor octene.

In a steady-state operation, an aqueous solution containing 0.660 kg/h of acrylic acid was obtained from the tower bottom and a gas containing 0.020 kg/h of acrylic acid was released from the tower top. The acrylic acid content in the released gas was higher by one figure than that in Example 1.

COMPARATIVE EXAMPLE 2

An operation of collecting acrylic acid from the mixed gas mentioned in Example 1 was conducted in the same manner as in Example 1 except that the aqueous collecting agent used in Example 1 was replaced by an aqueous solution containing 4.8% by weight of acrylic acid but containing neither acetic acid nor octene.

In a steady-state operation, an aqueous solution containing 0.657 kg/h of acrylic acid was obtained from the tower bottom and a gas containing 0.023 kg/h of acrylic acid was released from the tower top. The acrylic acid content in the released gas was higher by one figure than that in Example 1.

EXAMPLE 2

The aqueous acrylic acid solution obtained in Example 1 as the bottom solution of the acrylic acid-collecting tower was introduced into an azeotropic distillation tower to conduct azeotropic distillation. The azeotropic distillation tower had 60 sieve plates (plate-to-plate distance: 147 mm) and were provided with a distillate pipe at the top, a raw material-feeding pipe at the center and a bottom solution-drawing pipe at the bottom. The azeotropic distillation was conducted using octene as a solvent for azeotropic distillation while controlling the tower top pressure at 140 mmHg, the reflux ratio (total moles of reflux per unit time/total moles of distillate per unit time) at 0.42, and the amount of raw material fed at 8.12 l/h.

The distillate from the top of the azeotropic distillation tower was introduced into a storage tank to separate it into an organic phase and an aqueous phase. In a steady-state operation, the aqueous phase contained 4.8% by weight of acrylic acid, 8.0% by weight of acetic acid and 0.01% by weight of octene. The solution drawn out from the bottom of the azeotropic distillation tower contained 97.0% by weight of acrylic acid, 0.07% by weight of acetic acid, 0.02% by weight of water and 2.91% by weight of other substances. The octene content in the solution was below the detection limit (1 ppm).

The above aqueous phase was circulated into the acrylic acid-collecting tower of Example 1 and used as an aqueous collecting agent. As a result, in a steady-state operation, an aqueous solution containing 0.674 kg/h of acrylic acid was obtained from the tower bottom and a gas containing 0.006 kg/h of acrylic acid was released from the tower top.

EXAMPLE 3

An operation of collecting acrylic acid from the mixed gas mentioned in Example 1 was conducted in the same manner as in Example 1 except that the aqueous collecting agent used in Example 1 was replaced by an aqueous solution containing 4.2% by weight of acrylic acid, 8.2% by weight of acetic acid and 0.1% by weight of ethylbenzene.

In a steady-state operation, an aqueous solution containing 0.675 kg/h of acrylic acid was obtained from the tower bottom and a gas containing 0.005 kg/h of acrylic acid was released from the tower top.

EXAMPLE 4

Azeotropic distillation was conducted in the same manner as in Example 2 except that ethylbenzene was used as a solvent for azeotropic distillation and the reflux ratio was changed to 0.46. Also, acrylic acid collection in acrylic acid-collecting tower was conducted in the same manner as in Example 2.

The distillate from the top of the azeotropic distillation tower was introduced into a storage tank to separate it into an organic phase and an aqueous phase. In a steady-state operation, the aqueous phase contained 4.2% by weight of acrylic acid, 8.2% by weight of acetic acid and 0.1% by weight of ethylbenzene. The solution drawn out from the bottom of the azeotropic distillation tower contained 97.2% by weight of acrylic acid, 0.06% by weight of acetic acid, 0.02% by weight of water and 2.72% by weight of other substances. The ethylbenzene content in the solution was below the detection limit (1 ppm).

The above aqueous phase was circulated into the acrylic acid-collecting tower of Example 3 and used as an aqueous collecting agent. As a result, in a steady-state operation, an aqueous solution containing 0.675 kg/h of acrylic acid was obtained from the tower bottom and a gas containing 0.005 kg/h of acrylic acid was released from the tower top.

EXAMPLE 5

An operation of collecting acrylic acid from the mixed gas mentioned in Example 1 was conducted in the same manner as in Example 1 except that the aqueous collecting agent used in Example 1 was replaced by an aqueous solution containing 3.2% by weight of acrylic acid, 7.9% by weight of acetic acid and 0.1% by weight of toluene.

In a steady-state operation, an aqueous solution containing 0.673 kg/h of acrylic acid was obtained from the tower bottom and a gas containing 0.007 kg/h of acrylic acid was released from the tower top.

EXAMPLE 6

Azeotropic distillation was conducted in the same manner as in Example 2 except that toluene was used as a solvent for azeotropic distillation and the reflux ratio was changed to 1.35. Also, acrylic acid collection in acrylic acid-collecting tower was conducted in the same manner as in Example 2.

The distillate from the top of the azeotropic distillation tower was introduced into a storage tank to separate it into an organic phase and an aqueous phase. In a steady-state operation, the aqueous phase contained 3.2% by weight of acrylic acid, 7.9% by weight of acetic acid and 0.1% by weight of toluene. The solution drawn out from the bottom of the azeotropic distillation tower contained 97.5% by weight of acrylic acid, 0.03% by weight of acetic acid, 0.02% by weight of water and 2.45% by weight of other substances. The toluene content in the solution was below the detection limit (1 ppm).

The above aqueous phase was circulated into the acrylic acid-collecting tower of Example 5 and used as an aqueous collecting agent. As a result, in a steady-state operation, an aqueous solution containing 0.673 kg/h of acrylic acid was obtained from the tower bottom and a gas containing 0.007 kg/h of acrylic acid was released from the tower top.

EXAMPLE 7

An operation of collecting acrylic acid from the mixed gas mentioned in Example 1 was conducted in the same manner as in Example 1 except that the aqueous collecting agent used in Example 1 was replaced by an aqueous solution containing 1.8% by weight of acrylic acid, 7.5% by weight of acetic acid and 0.1% by weight of toluene.

In a steady-state operation, an aqueous solution containing 0.673 kg/h of acrylic acid was obtained from the tower bottom and a gas containing 0.008 kg/h of acrylic acid was released from the tower top.

EXAMPLE 8

Azeotropic distillation was conducted in the same manner as in Example 2 except that toluene was used as a solvent for azeotropic distillation and the reflux ratio was changed to 1.43. Also, acrylic acid collection in acrylic acid-collecting tower was conducted in the same manner as in Example 2.

The distillate from the top of the azeotropic distillation tower was introduced into a storage tank to separate it into an organic phase and an aqueous phase. In a steady-state operation, the aqueous phase contained 1.8% by weight of acrylic acid, 7.5% by weight of acetic acid, 0.1% by weight of toluene and 0.01% by weight of heptane. The solution drawn out from the bottom of the azeotropic distillation tower contained 97.5% by weight of acrylic acid, 0.03% by weight of acetic acid, 0.02% by weight of water and 2.35% by weight of other substances. The toluene content in the solution was below the detection limit (1 ppm).

The above aqueous phase was circulated into the acrylic acid-collecting tower of Example 7 and used as an aqueous collecting agent. As a result, in a steady-state operation, an aqueous solution containing 0.673 kg/h of acrylic acid was obtained from the tower bottom and a gas containing 0.007 kg/h of acrylic acid was released from the tower top.

EXAMPLE 9

An operation of collecting acrylic acid from the mixed gas mentioned in Example 1 was conducted in the same manner as in Example 1 except that the aqueous collecting agent used in Example 1 was replaced by an aqueous solution containing 2.9% by weight of acrylic acid, 8.2% by weight of acetic acid, 0.1% by weight of ethylbenzene and 0.01% by weight of heptane.

In a steady-state operation, an aqueous solution containing 0.673 kg/h of acrylic acid was obtained from the tower bottom and a gas containing 0.007 kg/h of acrylic acid was released from the tower top.

EXAMPLE 10

Azeotropic distillation was conducted in the same manner as in Example 2 except that a mixed solvent of ethylbenzene and heptane (mixing ratio=80:20 by weight) was used as a solvent for azeotropic distillation and the reflux ratio was changed to 0.55. Also, acrylic acid collection in acrylic acid-collecting tower was conducted in the same manner as in Example 2.

The distillate from the top of the azeotropic distillation tower was introduced into a storage tank to separate it into an organic phase and an aqueous phase. In a steady-state operation, the aqueous phase contained 2.9% by weight of acrylic acid, 8.2% by weight of acetic acid, 0.1% by weight of ethylbenzene and 0.01% by weight of heptane. The solution drawn out from the bottom of the azeotropic distillation tower contained 97.2% by weight of acrylic acid, 0.06% by weight of acetic acid, 0.02% by weight of water and 2.72% by weight of other substances. The content of ethylbenzene and heptane in the solution was below the detection limit (1 ppm).

The above aqueous phase was circulated into the acrylic acid-collecting tower of Example 9 and used as an aqueous collecting agent. As a result, in a steady-state operation, an aqueous solution containing 0.674 kg/h of acrylic acid was obtained from the tower bottom and a gas containing 0.006 kg/h of acrylic acid was released from the tower top.

EXAMPLE 11

An operation of collecting acrylic acid from the mixed gas mentioned in Example 1 was conducted in the same manner as in Example 1 except that the aqueous collecting agent used in Example 1 was replaced by an aqueous solution containing 1.5% by weight of acrylic acid, 7.9% by weight of acetic acid, 0.08% by weight of toluene and 0.01% by weight of heptane.

In a steady-state operation, an aqueous solution containing 0.672 kg/h of acrylic acid was obtained from the tower bottom and a gas containing 0.008 kg/h of acrylic acid was released from the tower top.

EXAMPLE 12

Azeotropic distillation was conducted in the same manner as in Example 2 except that a mixed solvent of toluene and heptane (mixing ratio=80:20 by weight) was used as a solvent for azeotropic distillation and the reflux ratio was changed to 1.41. Also, acrylic acid collection in acrylic acid-collecting tower was conducted in the same manner as in Example 2.

The distillate from the top of the azeotropic distillation tower was introduced into a storage tank to separate it into an organic phase and an aqueous phase. In a steady-state operation, the aqueous phase contained 1.5% by weight of acrylic acid, 7.9% by weight of acetic acid, 0.08% by weight of toluene and 0.01% by weight of heptane. The solution drawn out from the bottom of the azeotropic distillation tower contained 97.5% by weight of acrylic acid, 0.05% by weight of acetic acid, 0.02% by weight of water and 2.43% by weight of other substances. The content of toluene and heptane in the solution was below the detection limit (1 ppm).

The above aqueous phase was circulated into the acrylic acid-collecting tower of Example 11 and used as an aqueous collecting agent. As a result, in a steady-state operation, an aqueous solution containing 0.672 kg/h of acrylic acid was obtained from the tower bottom and a gas containing 0.008 kg/h of acrylic acid was released from the tower top.

EXAMPLE 13

An operation of collecting acrylic acid from the mixed gas mentioned in Example 1 was conducted in the same manner as in Example 1 except that the aqueous collecting agent used in Example 1 was replaced by an aqueous solution containing 0.8% by weight of acrylic acid, 7.5% by weight of acetic acid, 0.07% by weight of toluene and 0.01% by weight of heptane.

In a steady-state operation, an aqueous solution containing 0.671 kg/h of acrylic acid was obtained from the tower bottom and a gas containing 0.009 kg/h of acrylic acid was released from the tower top.

EXAMPLE 14

Azeotropic distillation was conducted in the same manner as in Example 2 except that a mixed solvent of toluene and heptane (mixing ratio=60:40 by weight) was used as a solvent for azeotropic distillation and the reflux ratio was changed to 1.75. Also, acrylic acid collection in acrylic acid-collecting tower was conducted in the same manner as in Example 2.

The distillate from the top of the azeotropic distillation tower was introduced into a storage tank to separate it into an organic phase and an aqueous phase. In a steady-state operation, the aqueous phase contained 0.8% by weight of acrylic acid, 7.5% by weight of acetic acid, 0.07% by weight of toluene and 0.01% by weight of heptane. The solution drawn out from the bottom of the azeotropic distillation tower contained 97.3% by weight of acrylic acid, 0.06% by weight of acetic acid, 0.02% by weight of water and 2.62% by weight of other substances. The content of toluene and heptane in the solution was below the detection limit (1 ppm).

The above aqueous phase was circulated into the acrylic acid-collecting tower of Example 13 and used as an aqueous collecting agent. As a result, in a steady-state operation, an aqueous solution containing 0.672 kg/h of acrylic acid was obtained from the tower bottom and a gas containing 0.008 kg/h of acrylic acid was released from the tower top.

What is claimed is:

1. A process for production of acrylic acid, which comprises:

introducing, into an acrylic acid-collecting tower, a mixed gas obtained by subjecting propylene and/or acrolein to catalytic gas-phase oxidation with a molecular oxygen-containing gas, and contacting the mixed gas with an aqueous collecting agent containing 0.5–5.0% by weight of acrylic acid, 3.0–10.0% by weight of acetic acid and 0.01–0.5% by weight of a poorly-soluble-in-water solvent, to form an aqueous acrylic acid solution, introducing the aqueous acrylic acid solution into an azeotropic distillation tower and subjecting the solution to azeotropic distillation using a poorly-soluble-in-water solvent, to obtain, from the tower bottom, acrylic acid substantially free from acetic acid, water or the poorly-soluble-in-water solvent and distil off, from the tower top, a mixture containing acetic acid, acrylic acid, water and the poorly-soluble-in-water solvent, introducing the mixture distilled off from the tower top, into a storage tank to separate it into an organic phase composed substantially of the poorly-soluble-in-water solvent and an aqueous phase containing acrylic acid, acetic acid, the poorly-soluble-in-water solvent and water, and circulating the organic phase into the azeotropic distillation tower.

2. A process according to claim 1, wherein the aqueous phase separated in the storage tank is circulated into the acrylic acid-collecting tower to use it as an aqueous collecting agent.

3. A process according to claim 1, wherein the poorly-soluble-in-water solvent is at least one solvent selected from the group consisting of aliphatic hydrocarbons having 7–8 carbon atoms, aromatic hydrocarbons having 7–8 carbon atoms and halogenated hydrocarbons having 2–6 carbon atoms.

4. A process according to claim 1, wherein the mixed gas introduced into the acrylic acid-collecting tower contains 10–20% by weight of acrylic acid, 0.2–1.0% by weight of acetic acid and 5–15% by weight of water.

5. A process according to claim 1, wherein the aqueous acrylic acid solution introduced into the azeotropic distillation tower contains 50–80% by weight of acrylic acid, 1–5% by weight of acetic acid and 20–40% by weight of water.

* * * * *

UNITED STATES PATENT AND TRADEMARK OFFICE
CERTIFICATE OF CORRECTION

PATENT NO. : 5,785,821
DATED : July 28, 1998
INVENTOR(S) : Kazuhiko Sakamoto et al.

It is certified that error appears in the above-identified patent and that said Letters Patent is hereby corrected as shown below:

Column 2,
Line 9, delete "or", insert -- and --.

Column 4,
Line 5, delete "very".
Line 26, after "ethylcyclohexane," insert -- octene --.

Column 7,
Line 44, delete "and 0.01% by weight of heptane"

Column 10,
Line 15, delete "or", insert -- and --.
Line 44, delete "water", insert -- steam --.

Signed and Sealed this

Twentieth Day of January, 2004

JON W. DUDAS
*Acting Director of the United States Patent and Trademark Office*

UNITED STATES PATENT AND TRADEMARK OFFICE
CERTIFICATE OF CORRECTION

PATENT NO. : 5,785,821
DATED : July 28, 1998
INVENTOR(S) : Kazuhiko Sakamoto et al.

It is certified that error appears in the above-identified patent and that said Letters Patent is hereby corrected as shown below:

Column 2,
Line 9, delete "or", insert -- and --.

Column 4,
Line 5, delete "very".
Line 26, after "ethylcyclohexane," insert -- octene --.

Column 7,
Line 44, delete "and 0.01% by weight of heptane"

Column 10,
Line 16, delete "or", insert -- and --.
Line 41, delete "water", insert -- steam --.

This certificate supersedes Certificate of Correction issued January 20, 2004.

Signed and Sealed this

Sixth Day of April, 2004

JON W. DUDAS
*Acting Director of the United States Patent and Trademark Office*